(12) United States Patent
Crowley (10) Patent No.: US 12,011,187 B2
(45) Date of Patent: Jun. 18, 2024

(54) SHEATH FOR CATHETER LENGTH ADJUSTMENT

(71) Applicant: OLYMPUS AMERICA INC., Center Valley, PA (US)

(72) Inventor: Peter J. Crowley, Norfolk, MA (US)

(73) Assignee: Olympus America Inc., Center Valley, PA (US)

( * ) Notice: Subject to any disclaimer, the term of this patent is extended or adjusted under 35 U.S.C. 154(b) by 89 days.

(21) Appl. No.: 17/583,887

(22) Filed: Jan. 25, 2022

(65) Prior Publication Data

US 2022/0233205 A1 Jul. 28, 2022

Related U.S. Application Data (60) Provisional application No. 63/141,705, filed on Jan. 26, 2021.

(51) Int. Cl.
| | | |
|---|---|---|
| A61B 1/307 | (2006.01) | |
| A61B 17/221 | (2006.01) | |
| A61B 1/018 | (2006.01) | |
| A61B 17/00 | (2006.01) | |

(52) U.S. Cl.
CPC ............ *A61B 17/221* (2013.01); *A61B 1/307* (2013.01)

(58) Field of Classification Search
CPC . A61B 1/307; A61B 1/00066; A61B 1/00121; A61B 17/221; A61B 2017/003; A61B 2017/00318; A61B 2017/00323; A61B 2017/00331; A61B 2046/234; A61M 39/1011; A61M 2025/0681
See application file for complete search history.

(56) References Cited

U.S. PATENT DOCUMENTS

| | | | | |
|---|---|---|---|---|
| 5,910,129 A | * | 6/1999 | Koblish | A61B 18/1492 604/525 |
| 7,300,415 B2 | * | 11/2007 | McMurtry | A61M 25/104 604/96.01 |
| 2013/0225943 A1 | * | 8/2013 | Holsing | G06T 7/12 600/409 |
| 2016/0095510 A1 | * | 4/2016 | Oskin | A61B 1/00128 600/125 |
| 2016/0278616 A1 | * | 9/2016 | Viebach | A61B 1/00066 |
| 2017/0291008 A1 | * | 10/2017 | Hillukka | A61M 25/0147 |
| 2021/0008344 A1 | * | 1/2021 | Chen | A61F 2/2436 |

* cited by examiner

*Primary Examiner* — Katherine M Rodjom
*Assistant Examiner* — Lindsey R. Rivers
(74) *Attorney, Agent, or Firm* — Schwegman Lundberg & Woessner, P.A.

(57) ABSTRACT

A sheath for guiding and controlling a length of a catheter, the sheath comprising a body defining a longitudinal axis. The body can include a proximal portion and a distal portion, a bore extending along the longitudinal axis between and through the proximal portion and the distal portion, and a looped portion located between the proximal portion and the distal portion.

14 Claims, 4 Drawing Sheets

SHEATH FOR CATHETER LENGTH ADJUSTMENT

CLAIM OF PRIORITY

This patent application claims the benefit of priority to U.S. Provisional Application Ser. No. 63/141,705, filed Jan. 26, 2021, which is incorporated by reference herein in its entirety.

TECHNICAL FIELD

The present application pertains generally, but not by way of limitation, to devices and methods for urology or other percutaneous medical procedures.

BACKGROUND

A ureteroscopy procedure can be performed to remove one or more kidney stones (or "calculi") from a patient's urinary tract, through the insertion, and subsequent removal, of a ureteroscope and other endoscopic devices through a patient's bladder, ureter, and one or more kidneys. Alternatively, a percutaneous nephrolithotomy ("PCNL") can be performed to remove one or more calculi from within a patient's kidney, ureter, etc.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims.

Endoscopes can be used to visualize or extract target masses from various regions of a patient's body, such as the urinary system, gallbladder, nasal passages, gastrointestinal tract, stomach, or tonsils. An endoscope can include one or more features, such as a camera, a light, a laser, and one or more working channels (e.g., a suction channel, an irrigation channel, or both). Various endoscopic methods utilizing different types of endoscopes can be used to remove calculi from a patient's urinary tract. One common example is a ureteroscopy. During a ureteroscopy, a ureteroscope can be inserted into a patient through the bladder, ureter, and into a calyx of a kidney to access a target site. A retrieval device, such as a balloon or basket catheter, a forceps, or other devices, can be inserted through, and advanced beyond, the working channel of the ureteroscope, such as to capture and retain one or more calculi identified for removal.

The retrieval device can also often be opened or closed, made with a malleable cage or structure, or otherwise configured to help to retain the captured one or more calculi. The retrieval device can then be withdrawn through the working channel of the ureteroscope, with one or more calculi retained therein. Retrieval devices commonly include an outer sheath to protect the retrieval device, during proximal and distal translation within the working channel of the ureteroscope. Additionally, if a particular calculus has a greater diameter than the working channel of the ureteroscope, the calculus can alternatively be ablated into smaller fragments with, for example, a laser incorporated into the distal end of the ureteroscope. The smaller fragments can then be captured with the retrieval device and withdrawn through the working channel of the ureteroscope.

A PCNL procedure is also commonly performed to remove calculi from within a patient's kidney, ureter, etc. A nephroscope can be inserted directly into the upper ureter, or a calyx of a kidney. An access incision can be made in a patient, which can extend percutaneously between, for example, a target site, such an upper portion of the ureter or a calyx of a kidney, and an outer surface of a patient's skin. The calculus can then be removed in a manner similar to a ureteroscopy procedure, such as by passing a retrieval device including a protective sheath through a working channel of the nephroscope to capture and retain one or more calculi identified for removal. The procedure can also include ablating a particular calculus into smaller fragments using various ablation methods.

A PCNL procedure can access a target site via a significantly shorter pathway, relative to a ureteroscopy procedure, and a retrieval device, such as a basket catheter configured for a ureteroscopy procedure, can be significantly longer than a basket catheter configured for a PCNL procedure. As a result, a basket catheter configured for one such procedure may not be suitable for use in another type of procedure, due to the significantly different length configurations often used in different medical procedures. Therefore, while different catheters may share common features such as a basket assembly, among others, any common features cannot be exploited without using an entirely different basket catheter, such as including a different part or sku number, etc.

For example, a physician currently cannot utilize a basket catheter configured for endoscopic use in a PCNL procedure, as a physician would have to perform the procedure with one or more hands positioned significantly farther away from a patient. This can interfere with a physician's ability to guide the catheter in a precise and accurate manner. Further, a physician would additionally have to manage an excess length of the basket catheter when performing other aspects of the procedure. Accordingly, as retrieval devices configured for ureteroscopy procedures are too long for practical use in PCNL procedures, a physician currently needs to first obtain and use a shorter retrieval device in order to perform a PCNL procedure. It would thus be desirable, at least from a cost and inventory standpoint, to eliminate the current necessity of purchasing and storing multiple different basket catheters.

This disclosure can help to address these issues, among others, such as by providing an endoscopic sheath capable of eliminating the need for different retrieval devices to perform various types of endoscopic procedures, such a ureteroscopy and a PCNL procedure. Such a sheath can help reduce the cost of various endoscopic procedures. For example, the sheath can define an operable feature capable of reducing a linear dimension of a retrieval device, such as a catheter. The sheath can further be configured to allow a physician's hands to be placed or otherwise positioned similarly, relative to a patient, as when performing various other endoscopic procedures. This can help to increase the ease of performing certain procedures and can also help to reduce the difficulty in transitioning between performing different types of endoscopic procedures.

Moreover, the sheath can also include the protective external packaging in which a catheter is sold and shipped inside. This can help reduce packaging waste and further decrease the cost of an endoscopic procedure. Additionally, the sheath can also be a component of a steerable catheter assembly. For example, a proximal portion of the sheath can be coupled to a handle. The handle can include a translatable actuator configured to allow a user to selectively cause a distal portion of the sheath to deflect or curve away from a proximal portion of the sheath, such as to help to navigate tortious internal anatomy of a patient, such as by adding a third dimension of control and access.

The above overview is intended to provide an overview of subject matter of the present patent application. It is not intended to provide an exclusive or exhaustive explanation of the invention. The description below is included to provide further information about the present patent application. While the following examples are discussed with a focus toward endoscopic urology procedures, the sheath can also be used in various other endoscopic procedures, such as in an endoscopic retrograde cholangiopancreatography ("ERCP") for biliary and pancreatic calculi removal. The sheath could also be used in non-endoscopic procedures, such as in laparoscopic procedures or otherwise in general surgery.

Figure 1:
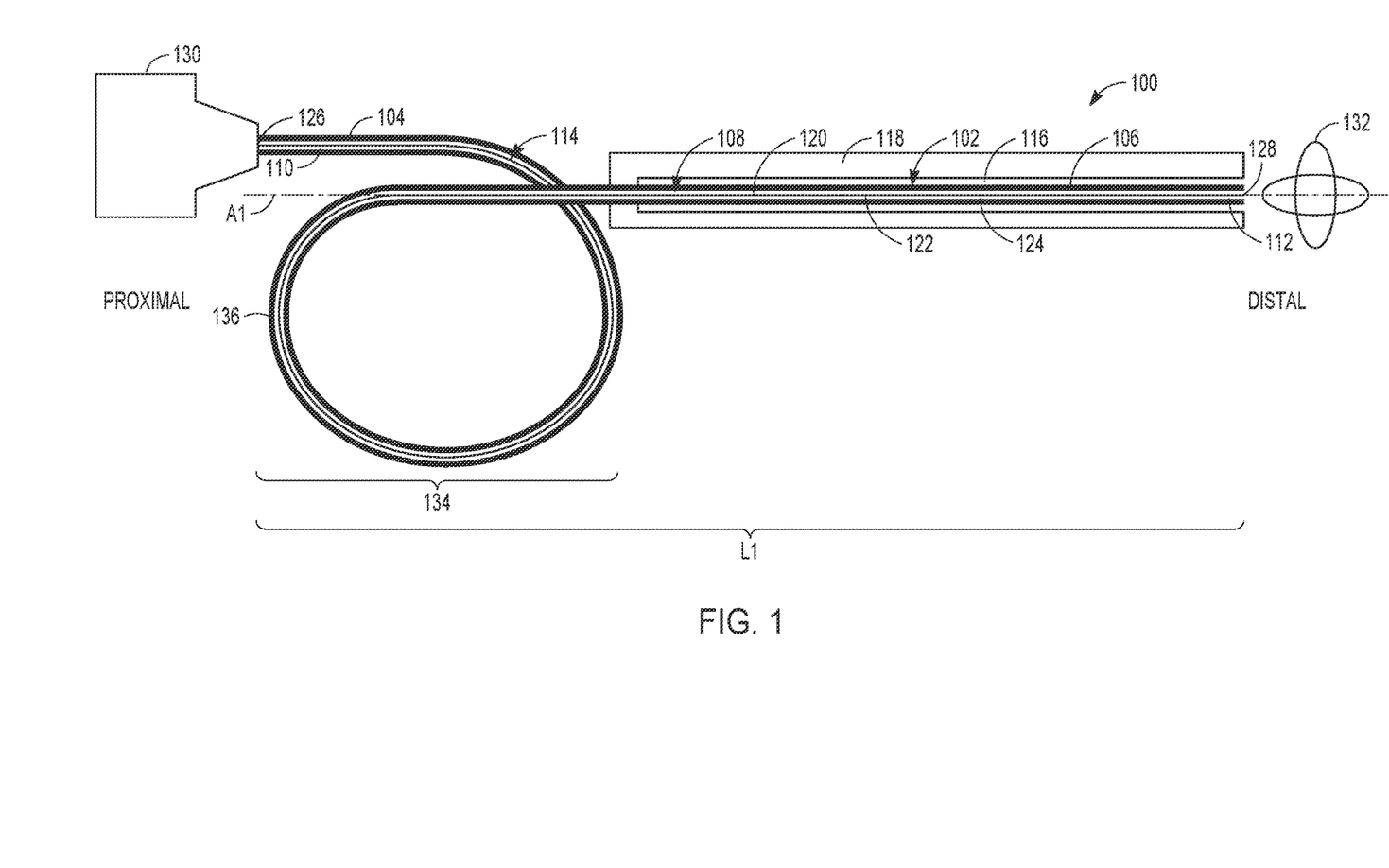
FIG. 1 illustrates a cross-section of an example of a catheter assembly.

FIG. 1 illustrates a cross-section of an example of a catheter assembly 100. FIG. 1 includes a dashed line corresponding to a longitudinal axis A1, and orientation indicators "Proximal" and "Distal". As illustrated in FIG. 1, the catheter assembly 100 can include a sheath 102. The sheath can be an elongate, rigid, or otherwise semi-rigid member. The sheath 102 can be generally cylindrical in shape. The sheath 102 can include a proximal portion 104 and a distal portion 106. The proximal portion 104 and the distal portion 106 can generally be opposite proximal and distal portions of the sheath 102, respectively.

A segment of the sheath 102 can define the longitudinal axis A1. For example, various segments of the proximal portion 104 or the distal portion 106 can extend along the longitudinal axis A1. The sheath 102 can define a bore 108 extending longitudinally within the sheath 102. The bore 108 can extend between and through the proximal portion 104 and the distal portion 106. The bore 108 can include a proximal end 110 and a distal end 112. The bore 108 can be configured to receive various endoscopic devices. For example, the bore 108 can be sized and shaped to receive a catheter 114.

The catheter 114 can be any variety of existing endoscopic catheters, such as a balloon or wire-basket catheter. The catheter 114 can extend within the sheath 102 between the proximal portion 104 and the distal portion 106. For example, when positioned within the bore 108, the sheath 102 can radially, or otherwise laterally, encompass the catheter 114. FIG. 1 also shows a nephroscope 118, which can be fiber optic or digital; and can also be any variety of other endoscopic instruments, such as a ureteroscope. The catheter 114 can be configured to be received within a working channel 116 of a nephroscope 118. The sheath 102 can protect the catheter 114 during proximal and distal transition within the working channel 116 of the nephroscope 118.

The catheter 114 can include a body 120. The body 120 can define an outer body surface 122. The outer body surface 122 can generally be an outermost radial or circumferential surface of the catheter 114. The bore 108 can define an inner surface 124 that can generally be an innermost radial or circumferential surface of the bore of the sheath 102. When the catheter 114 is inserted into the bore 108, the outer body surface 122 of the catheter 114 can contact the inner surface 124 of the bore 108, to guide the catheter 114 proximally or distally through the bore 108.

The body 120 of the catheter 114 can include a proximal end 126 and a distal end 128. The proximal end 126 can be configured to be fixedly or detachably couplable to a handle 130. For example, the proximal end 126 can include one or more features configured to engage the handle 130 to couple the catheter 114 to the handle 130. The handle 130 can be configured to allow a user to intra-operatively manipulate the catheter 114 from a location external to the patient.

The distal end 128 of the body 120 can be coupled to, or can otherwise comprise, a basket 132. The basket 132 can be configured to extend distally beyond the distal portion 106 of the sheath 102, such as for use in various aspects of an endoscopic procedure. For example, a physician can translate or otherwise operate one or more features of the handle 130, to extend the basket 132 beyond the distal end 112 of the bore 108, such as to open the basket 132. A physician can translate or otherwise operate one or more features of the handle 130, to retract the basket 132 within the bore 108 of the sheath 102, such as to close the basket 132.

The proximal portion 104 of the sheath 102 can also be configured to be fixedly or detachably couplable to the handle 130. For example, the proximal portion 104 can include one or more features configured to engage the handle 130 to couple the sheath 102 to the handle 130. The handle 130 can be configured to allow a user to intra-operatively manipulate the sheath 102 from a location external to the patient. The sheath 102 can define an operable feature 134. The operable feature 134 can be configured to reduce a linear dimension L1 of the catheter 114. The linear dimension L1 can be defined by a distance extending between the handle 130 and the basket 132 and can be generally parallel to the longitudinal axis A1. For example, the catheter 114 can be guided by, such as by extending through, the operable feature 134 to reduce the distance that the body 120 of the catheter 114 extends along the longitudinal axis A1.

As shown in FIG. 1, the operable feature 134 can generally be a looped portion 136. The looped portion 136 can be defined by a segment of the sheath 102 extending along a length of an arc deviating from the longitudinal axis A1. The looped portion 136 can be formed by the proximal portion 104 or the distal portion 106. The looped portion 136 can define a variety of shapes. For example, the looped portion 136 can define a substantially complete loop. The looped portion 136 can define, for example, a single loop, a double loop, or a variety of other multi-loop shapes, such as a three-dimensional coil or helical shape.

The looped portion 136 can generally begin and end at a point along the longitudinal axis A1. The looped portion 136 can also begin at a point along the longitudinal axis, but end at a position vertically or laterally offset from the longitudinal axis A1, such as to vertically or laterally offset the distal end 112 from the proximal end 110 of the bore 108. The looped portion 136 can have various dimensions, such as a radius. For example, the looped portion 136 can define a radius of about, but not limited to, 5-8 cm, a 9-10 cm, or an 11-15 cm. In examples where the looped portion 136 is a coil or other multi-loop shapes, the radius of each individual loop can be correspondingly or proportionally reduced relative to the number of complete loops defined by the looped portion 136.

The sheath 102 can be made from a material to allow a physician to manually alter the shape of the sheath 102. One such example is a heat moldable material, such as a thermoset or thermoplastic elastomer. For example, a physician can increase or decrease the radius of the looped portion 136 or by altering a single loop shape into a multi-loop shape. The catheter assembly 100, including the sheath 102 and the catheter 114, can configured to be disposable. The sheath 102 can be made by molding, swaging, extruding, or machining from any of a variety of materials, including but not limited to, rubber, plastic, silicone, or other polymers, such as Polytetrafluoroethylene ("PTFE"). The catheter assembly 100 can also be configured to be reusable. For example, after a procedure, the sheath 102, the catheter 114, or both, can be configured to be reprocessed, autoclaved, or otherwise sterilized for reuse in a subsequent procedure.

As such, the sheath 102, together with the catheter 114, can provide a number of benefits to both a patient and a physician. The sheath 102 can help reduce a need for separate catheter designs when performing different types of urology procedures, such as a ureteroscopy or a PCNL procedure. This can help to decrease the cost of a catheter, such as by making the catheter suitable for a wider variety of procedures, which can in turn decrease the cost of a urology procedure. The sheath 102 can also allow a physician to intra-operatively position their hands in a similar orientation, relative to a patient, when performing different types of urology procedures, using a single catheter.

The sheath 102 can be coupled to the handle 130, such as to provide for single user control. For example, a surgeon can operate the handle 130 to perform an endoscopic procedure or various aspects thereof using a single hand, or otherwise without the aid of a nurse or an assistant. The operable feature 134, in addition to the handle 130, can further increase control for a user. For example, by including a loop or coil shaped operable feature 134, a surgeon can grasp or otherwise engage both the handle 130 and the operable feature 134, such as with a single hand, during an endoscopic procedure. The catheter 114 can also be a steerable catheter to further aid a physician in navigating tortious anatomical pathways, while retaining the benefits set out above.

In the operation of one or more examples, the catheter assembly 100 can be purchased or shipped in a pre-assembled state, such as with the catheter 114 positioned within the bore 108 of the sheath 102. In this regard, the sheath 102 can comprise the protective packaging the catheter 114 is contained within, to further help reduce the cost of the catheter assembly 100 and a urology procedure and help to reduce waste.

Alternatively, the catheter 114 can be a pre-existing catheter. Such a pre-existing (or non-pre-packaged) catheter 114 can be inserted into the sheath 102 to help reduce a linear distance between a handle and a basket of the catheter, such as in preparation for a PCNL procedure. An access incision can be made in a flank region of a patient, and the nephroscope 118 can be extended through the access incision into and interior region of the ureter or a kidney.

A physician can use the nephroscope 118 to visualize and identify one or more calculi for removal. The catheter assembly 100 can then be inserted into the working channel 116 of the nephroscope 118. The handle 130 can be operated to translate the basket 132 distally beyond the distal portion 106 of the sheath 102, such as to open the basket 132. When the basket 132 is open, the basket 132 can be positioned to at least partially encompass one or more calculi, and the basket can subsequently be closed to capture and retain the one or more calculi, such as by operating the handle 130 to translate the basket 132 proximally. The catheter assembly 100, or various components thereof, can then be disposed of, or can be reprocessed or otherwise sterilized for reuse, along with the nephroscope 118.

Figure 2:
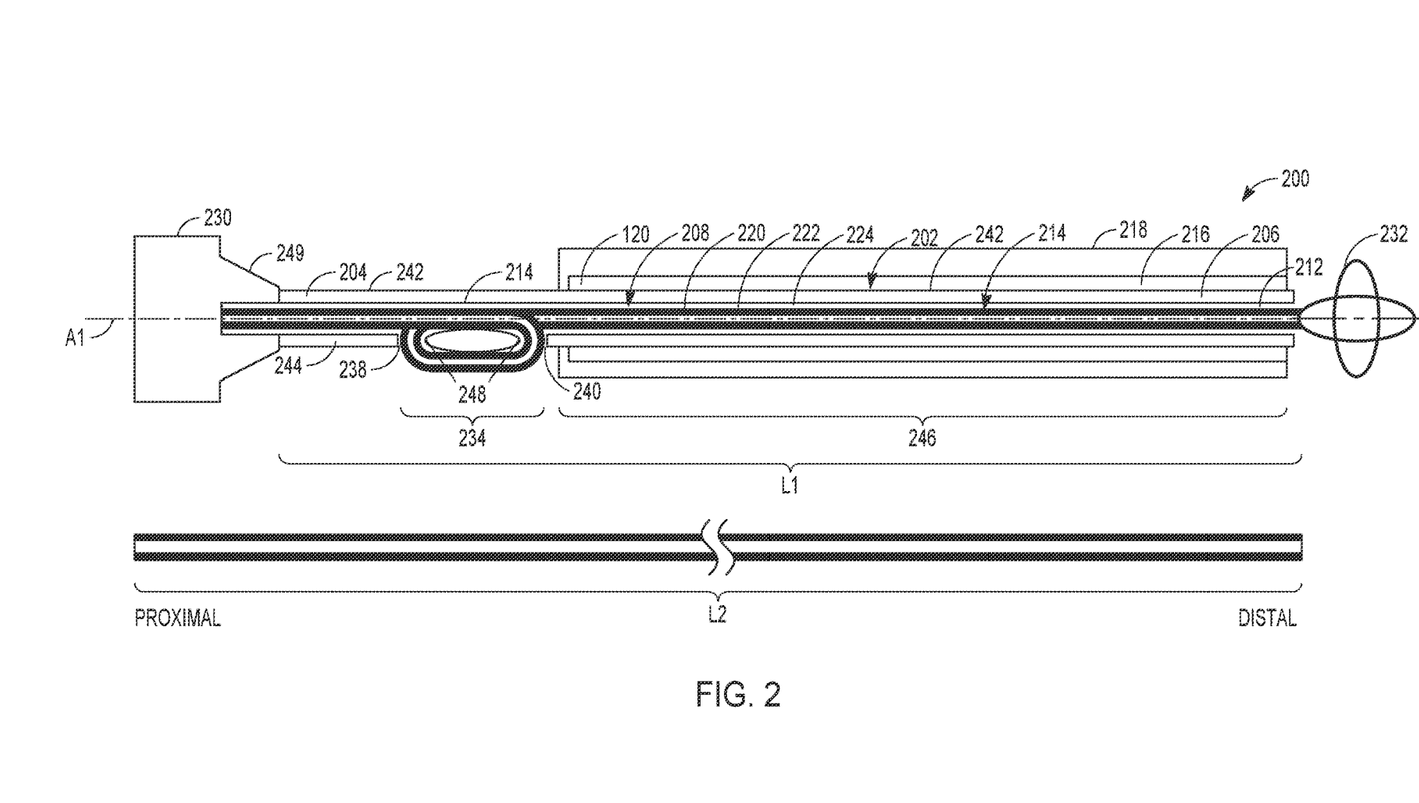
FIG. 2 illustrates a cross-section of an example of a catheter assembly.

FIG. 2 illustrates a cross-section of an example of a catheter assembly 200. Also shown in FIG. 2 is a dashed line corresponding to a longitudinal axis A1, and orientation indicators Proximal and Distal. As illustrated in FIG. 2, the catheter assembly 200 can be similar to the catheter assembly 100 shown in, and discussed with regard to FIG. 1; one difference in the catheter assembly 200 can be an operable feature 234 that can include a proximal aperture 238 and a distal aperture 240. Any of the catheter assemblies discussed above or below can be modified to include such features.

The sheath 202 can include an outer surface 242. The outer surface 242 can generally be an outermost radial or circumferential surface of the sheath 202. The sheath 202 can include a wall 244. The wall 244 can be defined as the vertical distance between the outer surface 242 of the sheath 202 and the inner surface 224 of the bore 208. The proximal aperture 238 and the distal aperture 240 can be, at least partially, circumferentially or can be peripherally formed in the sheath 202. The proximal aperture 238 and the distal aperture 240 can extend a lateral distance along the longitudinal axis A1. The proximal aperture 238 and the distal aperture 240 can extend transversely through the wall 244 of the sheath 202. The proximal aperture 238 and the distal aperture 240 can be formed in any of various lateral locations along the proximal portion 204 of the sheath 202. The proximal aperture 238 and the distal aperture 240 can also be sized and shaped relative to an outer diameter of the catheter 214.

The operable feature 234 can be configured to reduce the linear dimension L1 of the catheter 214, relative to an overall length L2 of the catheter 214. The linear dimension L1 can be defined by a distance the catheter 214 extends along the longitudinal axis A1, when received within the sheath 102, such as between the handle 230 and the basket 232. The overall length L2 can be defined by a distance the catheter 214 extends along the longitudinal axis A1, when the body 220 of the catheter 214 is oriented parallel to the longitudinal axis A1. For example, the catheter 214 can be guided, such as by extending through, the proximal aperture 238 and the distal aperture 240 to help reduce the linear dimension L1, relative to the overall length L2.

As shown in FIG. 2, the proximal aperture 238 and distal aperture 240 can allow a segment of the body 220 of the catheter 214 to extend outside of the sheath, such as to form a loop. For example, various segments or portions of the body 220 can extend distally through the bore 208 to the distal aperture 240, extend through the distal aperture to the outer surface 242 of the sheath 202, extend proximally along the outer surface 242 to the proximal aperture 238, extend through the proximal aperture 238 to the inner surface 224, and extend distally through the bore 208 to the distal end 212.

The operable feature 234, and the operable feature 134 shown in FIG. 1, can be configured to accommodate or otherwise correspond to a length of the catheter 214. For example, the catheter 214 can have of length of, but not limited to, about 25-30 cm, 31-40 cm, or 41-50 cm, such as to allow the catheter 214 to be used in a ureteroscopy procedure. The catheter 214 can define a working length 246. The working length 246 can be defined as the axial length the body 220 of the catheter is to be inserted into a patient, or to be inserted into the working channel 216 of the nephroscope 218 during a particular type of urology procedure.

The working length 246 can be reduced such as by configuring a lateral location of the proximal aperture 238 relative to a lateral location of the distal aperture 240, or by configuring one or more dimensions of a shape defined by the looped portion 136, to help reduce the linear dimension L1, relative to the overall length L2. For example, in one example of a PCNL procedure, the working length 246 can be about 15 cm. In such an example, the operable feature 234 or the operable feature 134 can be configured to reduce the working length 246 of the catheter 214 by, but not limited to, about 10-15 cm, 16-25 cm, or 26-35 cm.

Each of the proximal aperture 238 and the distal aperture 240 can also include a beveled edge 248. The beveled edge 248 of each of the proximal aperture 238 and the distal aperture 240 can be a chamfer, bevel, rounded, or otherwise shaped surface extending generally transversely between the inner surface 224 of the bore 208 and the outer surface 242 of the sheath 202. The beveled edge 248 of each of the proximal aperture 238 and the distal aperture 240 can help to prevent the body 220 of the catheter 214 from binding on the proximal aperture 238 or the distal aperture 240, such as when the catheter 214 is translated proximally or distally. The operable feature 234 can also include only the proximal aperture 238. For example, various segments of the body 220 of the catheter 214 can extend through the proximal aperture 238 to the outer surface 242 of the sheath 202, form one or more loops, extend back though the proximal aperture 238 to the inner surface 224 of the bore 208, and extend distally within the bore 208 to the distal end 212.

The sheath 202 can have various diameters. For example, the outer surface 242 of the sheath 202 can define a diameter of about, but not limited to, about 2-7 French (0.67-2.33 mm), 8-10 French (2.67-3.33 mm), 11-15 French (3.67-5 mm), or 16-30 French (5.33-10 mm). The body 220 of the catheter 214 can have various outer diameters. For example, the outer body surface 122 of the body 220 define an outer diameter of about, but not limited to, 1-2 French (0.33-0.67 mm), 3-4 French (1-1.33 mm), or 5-7 French (1.67-2.33 mm). The bore 208 can also have various diameters. For example, the inner surface 224 of the bore 208 can define a diameter of 4-9 French (1.33-3 mm), 10-12 French (3.33-4 mm), 14-16 French (4.67-5.33 mm), or 17-28 French (5.67-9.33 mm).

The sheath 202 can be made by molding, swaging, extruding, or machining from any of a variety of materials, including but not limited to, rubber, plastic, silicone, or other polymers, such as Polytetrafluoroethylene ("PTFE"). The sheath 202 can also include materials of variable hardness, such as measure by Shore A hardness. For example, the sheath 202 can be made from materials including durometers of about, but not limited to, 50-55a, 56a-60a, 61-69a, or 70a-80a.

The proximal portion 204 can be made from a softer durometer and the distal portion 206 can be made from a firmer durometer. For example, various distinct segments of the sheath 202 extending between the proximal portion 204 and the distal portion 206 can made of differing durometer materials. Alternatively, the sheath 202 can smoothly or gradually blend materials of differing durometers between the proximal portion 204 and the distal portion 206. A softer durometer can help to increase the flexibility of the distal portion 206 of the sheath 202, such as to improve the ability of the distal portion 206 of the sheath 202 to flex, for example, to improve the ease of insertion through tortuous anatomical pathways, such as a calyx of a kidney.

A firmer durometer can help to reduce deflection of the proximal portion 204, relative to the longitudinal axis A1, of the proximal portion 204 of the sheath 202, as the sheath 202 is translated through the working channel 216 of the nephroscope 218. A firmer durometer can also help to improve engagement with one or more features of the handle 230, such as a coupler 249, to more securely couple the proximal portion 204 of the sheath 202 to the handle 230. The term "durometer" can be the resistance of a material such as rubber or plastic to deformation or deflection. The sheath 202 can further include, or be coated with, a hydrophilic compound, such as to further improve the ease of insertion into a patient or through the working channel 216 of the nephroscope 218.

Figure 3A:
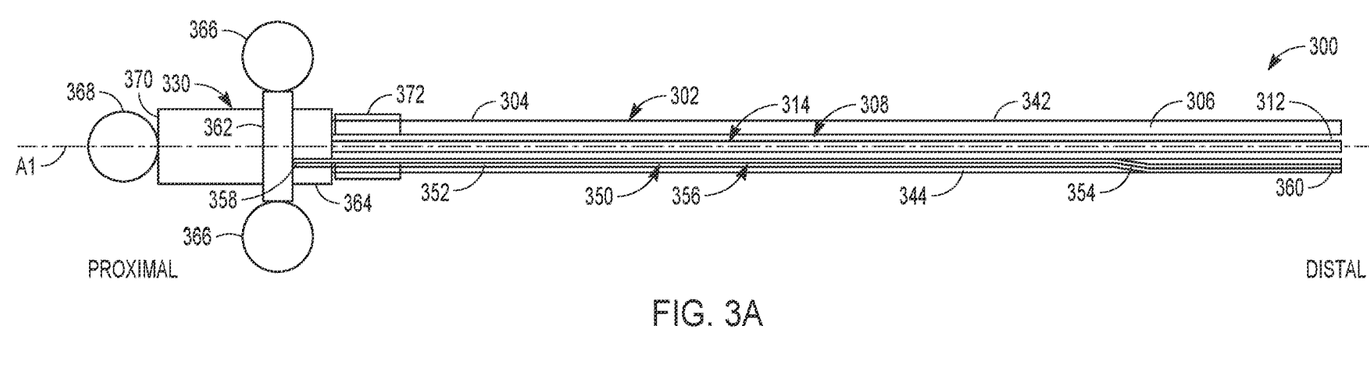
FIG. 3A illustrates a cross-section of an example of a steerable catheter assembly in a first position.
Figure 3B:
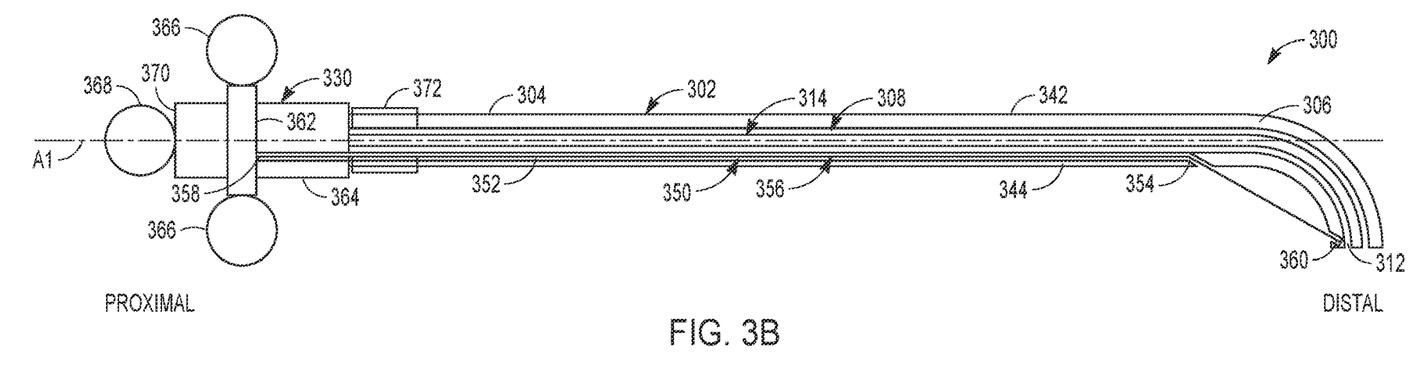
FIG. 3B illustrates a cross-section of an example of a steerable catheter assembly in a second position.

FIG. 3A illustrates a cross-section view of an example of a steerable catheter assembly 300 in a first position. FIG. 3B illustrates a cross-section of an example of a steerable catheter assembly 300 in a second position. Also shown in FIGS. 3A and 3B are dashed lines corresponding to a longitudinal axis A1, and orientation indicators Proximal and Distal. FIGS. 3A-3B are discussed below concurrently.

The steerable catheter assembly 300 can be similar to the catheter assembly 100 or the catheter assembly 200; one difference in the steerable catheter assembly 300 can be configured to allow the distal portion 306 of the sheath to be steerable intra-operatively, from a location external to a patient. The steerable catheter assembly 300 discussed can be modified to include either of the operable features 134 and 234 as shown in, and discussed with respect to, FIGS. 1-2.

The wall 344 of the sheath 302 can include a wire bore 350. The wire bore 350 can include a first portion 352 and a second portion 354. The first portion 352 can extend generally parallel to the longitudinal axis A1. The first portion 352 can extend longitudinally through the proximal portion 304 and at least partially through the distal portion 306 of the sheath 302. The second portion 354 can extend an angle to the longitudinal axis A1. The second portion 354 can extend through the wall 344 of the sheath 302, such as between the bore 308 and the outer surface 342.

The steerable catheter assembly 300 can include a wire 356. The wire 356 can include a first end 358 and a second end 360. The first end 358 and the second end 360 can generally be opposite proximal and distal portions of the wire 356, respectively. The wire 356 can be an elongate and flexible or semi-rigid, member. The wire 356 can be configured to be received within the wire bore 350. For example, the wire 356 can extend within the wire bore 350; and can extend longitudinally through the first portion 352. The wire 356 can extend through the second portion 354, and to, or along, at least a segment of the outer surface 342 of the sheath 302. The second end 360 of the wire 356 can be fixedly connected to a point located along the outer surface 342 of the sheath 302, such as at or near a distal end of the sheath 302.

The handle 330 can include an actuator 362. The actuator 362 can be any variety of mechanical actuators, such as, but not limited to, a slidable or a rotatable member. The actuator 362 can be coupled to the handle 330. For example, as shown in FIGS. 3A-3B, the actuator 362 can be a slidable member slidably coupled to, and can peripherally encompass at least a segment of, an outer surface 364 of the handle 330. The outer surface 364 can generally be an outermost surface of the handle 330. The first end 358 of the wire 356 can be fixedly connected to the actuator 362.

The actuator 362 can be translated proximally, to cause to the wire 356 to translate proximally within the wire bore 350, to thereby cause the distal portion 306 of the sheath 302 to curve, or otherwise deflect away, from the longitudinal axis A1. For example, the actuator 362 can be translated from a first position, such as illustrated in FIG. 3A, to a second position, such as illustrated in FIG. 3B. The first position can be a distal-most extension point of the actuator 362, and the second position can be a proximal-most extension point of the actuator 362. The actuator 362 can thereby precisely and selectively control a degree deflection away from the longitudinal axis A1.

The actuator 362 can be operated, for example, to cause the distal portion 306 of the sheath 302 to deflect from the longitudinal axis A1 such that the distal end 312 of the bore 308 extends at, but not limited to, about a 5-20, 21-40, 41-70, or 71-90 degree angle relative to the longitudinal axis A1. The actuator 362 can also include one or more gripping features 366. The gripping features 366 can be any variety of protrusions or other features extending outward from the actuator 362. The gripping features 366 configured to engage a user's fingers or hands, such as a closed-loop or a ring.

The handle 330 can also include a grip 368. The grip 368 can be similar to the gripping features 366 located on the actuator 362; one difference is that the grip 368 is located on a proximal end 370 of the handle 330. The proximal end 370 can generally be a proximal end of a housing or body of the handle 330. For example, a user can engage the gripping features 366 of the actuator 362, and the grip 368 of the handle 330, such as to help to apply a lateral force to the actuator 362, to translate the actuator 362 proximally toward the proximal end 370 of the handle 330.

In some examples, the steerable catheter assembly 300 can also include a lock 372. The lock 372 can be, or otherwise include, any variety of mechanical lock mechanisms, such as, but not limited to, a luer lock or another type of threaded lock, a gate valve or another type of compression lock, or a spring-loaded toggle or button. The lock 372 can generally be located between the handle 330 and the distal portion 306 of the sheath 302. The lock 372 can be configured to impede proximal and distal translation of the wire 356, such as to selectively retain a curvature or deflection angle of the distal portion 306 of the sheath 302. A feature of the lock 372 can either directly contact the wire 356, or apply pressure to and deform a segment of the wire bore 350 to contact the wire 356, to prevent either proximal or distal translation of the wire 356. For example, when the actuator 362 is located in the second position, the lock 372 can be operated to retain the actuator 362 in the second position, such as to help a user perform other aspects of a procedure.

Figure 4:
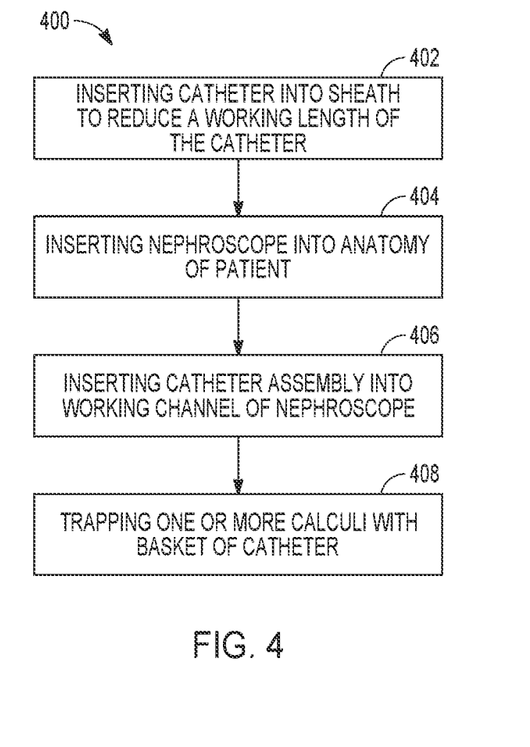
FIG. 4 illustrates an example of a method of extracting one or more calculi from a patient using a catheter assembly.

FIG. 4 illustrates an example of a method of extracting one or more calculi from a patient. In this example, the method 400 includes operations such as optionally inserting a catheter into a sheath at 402, inserting a nephroscope into a patient at 404, inserting a catheter assembly into the nephroscope at 406, and trapping one or more calculi at 408. The steps or operations of the method 400 are illustrated in a particular order for convenience and clarity; many of the discussed operations can be performed in a different sequence or in parallel without materially impacting other operations. Optionally, steps or operations of the method 400 can be omitted or performed multiple times. The method 400 as discussed includes operations that can be performed by multiple different actors, devices, and/or systems. It should be understood that subsets of the operations discussed in the method 400 can be attributable to a single actor, device, or system could be considered a separate standalone process or method.

In one or more examples, the method 400 can begin with optional operation 402. Operation 402 can include inserting a catheter into a bore of a sheath, wherein inserting the catheter into the bore causes the catheter to form a looped portion, to reduce a working length of the catheter.

For example, the sheath can define an operable feature, such as a looped portion, configured to reduce a linear dimension of the catheter, such as defined by a distance generally parallel to a longitudinal axis A1 and extending between a handle of the catheter at a proximal end of the catheter, and a basket at a distal end of the catheter, when the catheter is positioned within the sheath. The looped portion can be a single loop, a double loop, or a variety of other multi-loop shapes, such as a coil, helix, or other multi-loop shapes.

In one or more examples, operation 402 can alternatively include wherein inserting the catheter includes guiding the catheter through a distal aperture of the sheath to an outer surface of the sheath, guiding the catheter proximally along the outer surface, and guiding the catheter into the bore through a proximal aperture of the sheath. For example, alternatively to the looped portion, the operable feature of the sheath can comprise a proximal aperture and a distal aperture. A user can guide the catheter first through the bore, second through the distal aperture, third through the second aperture, and finally distally through the bore to a distal end of the bore, such as to form a loop.

In one or more examples, the method 400 can include operation 404, which can include inserting a nephroscope into anatomy of a patient. For example, operation 404 can include making an access incision in a patient, which can extend directly between an outer surface of the skin and, for example, the upper ureter or a calyx of a kidney. The nephroscope can then be inserted through access incision to reach a target site.

In one or more examples, operation 404 can include wherein inserting the catheter assembly into anatomy of a patient includes translating an actuator to cause a distal portion of the sheath to curve away from a longitudinal axis, to navigate internal anatomy of the patient. For example, the catheter assembly can include the sheath, the catheter, and a wire extending within a wall of the sheath between an actuator of a handle of the catheter, and a distal portion of the sheath. A user can translate the actuator proximally to, correspondingly, proximally translate the wire, to in turn cause the distal portion of the sheath to deflect or otherwise bend away from the longitudinal axis.

In one or more examples, the method 400 can include operation 406. Operation 406 can include inserting the catheter assembly into a working channel of the nephroscope. For example, a user can translate the catheter assembly distally within the working channel of the nephroscope to allow a basket of the catheter to reach the target site. In one or more examples, the method 400 can include operation 408. Operation 408 can include trapping one or more calculi with the basket of the catheter. For example, a user can operate the handle of the catheter, such as to open the basket.

A user can then position the basket such that the basket at least partially encompasses and traps one or more calculi, such as by operating the handle of the catheter to close the basket. The handle can be operated by a user, such as with a single hand, to allow a user to trap one or more calculi without the aid of a nurse or an assistant.

The steps or operations of the method 400 are illustrated in a particular order for convenience and clarity. The discussed operations can be performed in parallel or in a different sequence without materially impacting other operations. The method 400 as discussed includes operations that can be performed by multiple different actors, devices, and/or systems. It is understood that subsets of the operations discussed in the method 400 can be attributable to a single actor device, or system, and could be considered a separate standalone process or method.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure.

This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

NOTES AND EXAMPLES

Example 1 is a sheath for guiding and controlling a length of a catheter, the sheath comprising: a body defining a longitudinal axis, the body including: a proximal portion and a distal portion, the body defining a bore extending along the longitudinal axis between and through the proximal portion and the distal portion; and a looped portion located between the proximal portion and the distal portion.

In Example 2, the subject matter of Example 1 includes, wherein the looped portion of the body extends along a length of an arc deviating from the longitudinal axis, such that the looped portion defines at least one complete loop.

In Example 3, the subject matter of Examples 1-2 includes, wherein the looped portion of the body extends along a length of an arc deviating from the longitudinal axis, such that the looped portion defines at least two or more complete loops.

In Example 4, the subject matter of Examples 1-3 includes, wherein the looped portion of the body extends along a length of an arc deviating from the longitudinal axis, such that the looped portion defines a helical shape.

In Example 5, the subject matter of Examples 1-4 includes, wherein the sheath is made of a heat moldable material.

In Example 6, the subject matter of Examples 1-5 includes, wherein the distal portion of the catheter includes a material that is at least one of softer or more flexible than a material of a proximal portion of the sheath.

Example 7 is a catheter assembly for guiding and controlling a length of a catheter, the catheter assembly comprising: a catheter including an elongate catheter body and including an operable feature at a distal end of the catheter body; a sheath including: a body defining a longitudinal axis, the body including: a proximal portion and a distal portion, the body defining a bore extending along the longitudinal axis between and through the proximal portion and the distal portion, wherein the catheter extends within the bore between and through the proximal portion and to, or through, the distal portion of the body; and a proximal aperture and a distal aperture, each of the proximal and the distal apertures extending transversely through an outer surface of the body of the sheath into the bore, the catheter extending into the bore, exiting the body through the distal aperture, extending proximally along the outer surface, and extending into the bore through the proximal aperture.

In Example 8, the subject matter of Example 7 includes, wherein the catheter is one of a basket catheter or a balloon catheter.

In Example 9, the subject matter of Examples 7-8 includes, wherein a surface of the proximal aperture and a surface of the distal aperture are rounded or beveled.

Example 10 is a steerable catheter assembly comprising: a sheath defining a longitudinal axis and including a bore, the bore extending longitudinally within the sheath between and through a proximal portion and a distal portion the sheath, the sheath including a feature configured reduce a linear dimension of a catheter, when the catheter is positioned within the bore of the sheath; a catheter extending through the bore, the catheter including an operable feature configured to extend distally from the distal portion of the sheath; a handle connected to the proximal portion of the sheath, the handle coupled to a proximal portion of a wire and operable to cause the distal portion of the sheath to curve away from the longitudinal axis.

In Example 11, the subject matter of Example 10 includes, a wire including a first end and a second end, the first end the wire coupled to the handle and second end of the wire connected to an outer surface of the distal portion of the sheath, wherein the wire extends within and through a wall of the sheath.

In Example 12, the subject matter of Example 11 includes, wherein the handle includes an actuator connected to the first end of the wire and operable to be translated proximally, to pull the wire to cause the distal portion of the sheath to curve away from the longitudinal axis.

In Example 13, the subject matter of Examples 10-12 includes, wherein the operable feature is a loop formed by a portion of the sheath extending along a length of an arc deviating from the longitudinal axis, such that a portion of the sheath defines at least one complete loop.

In Example 14, the subject matter of Examples 10-13 includes, wherein the operable feature is a coil formed by a portion of the sheath extending along a length of an arc deviating from the longitudinal axis, such that a portion of the sheath defines at least two complete loops.

In Example 15, the subject matter of Examples 10-14 includes, wherein the operable feature comprises a proximal aperture and a distal aperture, each of the proximal and the distal apertures extending transversely through an outer surface of a body of the sheath into the bore, wherein the catheter extends into the bore, exits the body through the distal aperture, extends proximally along the outer surface, and extends into the bore through the proximal aperture.

In Example 16, the subject matter of Examples 10-15 includes, wherein the distal portion of the sheath includes a material that is at least one of softer or more flexible than a material of a proximal portion of the sheath.

In Example 17, the subject matter of Examples 11-16 includes, a lock operable to engage the wire to limit translation of the wire with respect to the sheath.

In Example 18, the subject matter of Example 17 includes, wherein the lock is a luer lock or a threaded lock.

In Example 19, the subject matter of Examples 17-18 includes, wherein the lock is a compression valve or a gate valve.

In Example 20, the subject matter of Examples 17-19 includes, wherein the lock is a spring-loaded toggle or button.

Example 21 is a method to implement any of Examples 1-20.

What is claimed is:

1. A catheter assembly for guiding and controlling a length of a catheter, the catheter assembly comprising:
   a catheter including an elongate catheter body and including an operable feature at a distal end of the catheter body, wherein the catheter is one of a basket catheter or a balloon catheter;
   a sheath including:
   a body defining a longitudinal axis, the body including:
   a proximal portion and a distal portion, the body defining a bore extending along the longitudinal axis between and through the proximal portion and the distal portion, wherein the catheter extends within the bore between and through the proximal portion and to, or through, the distal portion of the body; and
   a proximal aperture and a distal aperture, each of the proximal and the distal apertures extending transversely through an outer surface of the body of the sheath into the bore, the catheter extending into the bore, exiting the body through the distal aperture, extending proximally along the outer surface, and extending into the bore through the proximal aperture.

2. The assembly of claim 1, wherein a surface of the proximal aperture and a surface of the distal aperture are rounded or beveled.

3. The assembly of claim 1, wherein the sheath comprises a rigid material.

4. The assembly of claim 1, wherein the sheath is removable.

5. The assembly of claim 1, wherein the sheath is made of a heat moldable material.

6. The assembly of claim 1, wherein the distal portion of the catheter body includes a material that is at least one of softer or more flexible than a material of the sheath.

7. A steerable catheter assembly comprising:
   a sheath defining a longitudinal axis and including a bore, the bore extending longitudinally within the sheath between and through a proximal portion and a distal portion of the sheath, the sheath including a feature configured to reduce a linear dimension of a catheter, when the catheter is positioned within the bore of the sheath;
   a catheter extending through the bore,
   wherein the catheter includes an operable feature configured to extend distally from the distal portion of the sheath, and wherein the operable feature comprises a proximal aperture and a distal aperture, each of the proximal and the distal apertures extending transversely through an outer surface of a body of the sheath into the bore, wherein the catheter extends into the bore, exits the body through the distal aperture, extends proximally along the outer surface, and extends into the bore through the proximal aperture;
   a handle connected to the proximal portion of the sheath, the handle coupled to a proximal portion of a wire and operable to cause the distal portion of the sheath to curve away from the longitudinal axis.

8. The assembly of claim 7, further comprising a wire including a first end and a second end, the first end of the wire coupled to the handle and the second end of the wire connected to an outer surface of the distal portion of the sheath, wherein the wire extends within and through a wall of the sheath.

9. The assembly of claim 8, wherein the handle includes an actuator connected to the first end of the wire and operable to be translated proximally, to pull the wire to cause the distal portion of the sheath to curve away from the longitudinal axis.

10. The assembly of claim 7, wherein the distal portion of the sheath includes a material that is at least one of softer or more flexible than a material of a proximal portion of the sheath.

11. The assembly of claim 8, further comprising a lock operable to engage the wire to limit translation of the wire with respect to the sheath.

12. The assembly of claim 11, wherein the lock is a luer lock or a threaded lock.

13. The assembly of claim 11, wherein the lock is a compression valve or a gate valve.

14. The assembly of claim 11, wherein the lock is a spring-loaded toggle or button.

\* \* \* \* \*